(12) United States Patent
Zettier

(10) Patent No.: US 7,217,234 B2
(45) Date of Patent: May 15, 2007

(54) SYSTEM AND A METHOD FOR CONTROLLING A CENTRIFUGE FOR THE PRODUCTION OF A SKIMMED MILK PRODUCT

(75) Inventor: Karl-Heinz Zettier, Oelde (DE)

(73) Assignee: Westfalia Separator AGB, Oelde (DE)

( * ) Notice: Subject to any disclaimer, the term of this patent is extended or adjusted under 35 U.S.C. 154(b) by 426 days.

(21) Appl. No.: 10/484,029

(22) PCT Filed: Jul. 2, 2002

(86) PCT No.: PCT/EP02/07258

§ 371 (c)(1),
(2), (4) Date: Jan. 16, 2004

(87) PCT Pub. No.: WO03/007700

PCT Pub. Date: Jan. 30, 2003

(65) Prior Publication Data

US 2004/0187711 A1 Sep. 30, 2004

(30) Foreign Application Priority Data

Jul. 18, 2001 (DE) .................................. 101 35 073

(51) Int. Cl.
*A01J 11/10* (2006.01)
*B04B 13/00* (2006.01)

(52) U.S. Cl. ............................. 494/1; 494/10; 494/27; 494/37; 99/456; 426/231; 426/491

(58) Field of Classification Search .................... 494/1, 494/10, 23, 27, 37; 426/231, 491, 456, 586; 99/452, 456
See application file for complete search history.

(56) References Cited

U.S. PATENT DOCUMENTS

| 2,264,665 | A | * | 12/1941 | Hall ........................... 426/417 |
| 2,423,834 | A | * | 7/1947 | Horneman et al. ......... 426/417 |
| 2,542,456 | A | | 2/1951 | Ayers |
| 2,628,023 | A | * | 2/1953 | Dahlstedt ...................... 494/2 |
| 2,837,271 | A | * | 6/1958 | Haglund ...................... 494/10 |
| 3,379,370 | A | * | 4/1968 | Anderson ..................... 494/11 |
| 3,656,685 | A | * | 4/1972 | Kjellgren ..................... 494/42 |
| 3,829,584 | A | * | 8/1974 | Seiberling ................... 426/231 |
| 3,924,804 | A | * | 12/1975 | Niemeyer ..................... 494/37 |
| 3,946,113 | A | * | 3/1976 | Seiberling ................... 426/231 |
| 3,983,257 | A | * | 9/1976 | Malmberg et al. .......... 426/231 |

(Continued)

FOREIGN PATENT DOCUMENTS

DE 25 31 141 1/1977

(Continued)

*Primary Examiner*—Charles E. Cooley
(74) *Attorney, Agent, or Firm*—Barnes & Thornburg LLP

(57) ABSTRACT

The present disclosure includes a method of controlling a centrifuge for the centrifugal production of a milk product. The steps include taking a milk sample at an outlet of the centrifuge from a liquid phase, adding a substance to the milk sample that increases light transmittance of the milk sample, determining the light transmittance of the milk sample by transilluminating the milk sample using a light source and measuring light intensity via a photo cell, determining the fat content from a measurement of the light transmittance, and controlling the centrifuge as a function of the determination of the fat content. The present disclosure also includes a system for controlling the centrifuge.

17 Claims, 3 Drawing Sheets

U.S. PATENT DOCUMENTS

| | | | |
|---|---|---|---|
| 4,017,643 A * | 4/1977 | Lester | 426/231 |
| 4,074,622 A * | 2/1978 | Niemeyer | 99/456 |
| 4,075,355 A * | 2/1978 | Pato | 426/231 |
| 4,981,610 A | 1/1991 | Linden et al. | |
| 5,009,794 A * | 4/1991 | Wynn | 210/739 |
| 5,137,738 A * | 8/1992 | Wynn | 426/231 |
| 5,260,079 A * | 11/1993 | Zettier et al. | 426/231 |
| 5,591,469 A * | 1/1997 | Zettier | 426/231 |
| 5,928,702 A * | 7/1999 | Lidman et al. | 426/580 |

FOREIGN PATENT DOCUMENTS

| | | |
|---|---|---|
| DE | 35 39 485 | 5/1987 |
| DE | 3814761 A1 * | 11/1988 |
| DE | 40 17 398 | 11/1990 |
| DE | 42 18 555 | 12/1993 |
| DE | 43 02 165 C1 | 5/1994 |
| DE | 44 07 061 | 9/1995 |
| DE | 195 03 065 | 11/1995 |
| JP | 2-224624 * | 9/1990 |
| WO | 90/00862 A1 * | 2/1990 |
| WO | 99/57988 A1 * | 11/1999 |
| WO | WO 00/49388 | 8/2000 |
| WO | 03/007700 A1 * | 1/2003 |
| WO | 2005/065835 A1 * | 7/2005 |
| WO | 2005/086994 A1 * | 9/2005 |

* cited by examiner

SYSTEM AND A METHOD FOR CONTROLLING A CENTRIFUGE FOR THE PRODUCTION OF A SKIMMED MILK PRODUCT

CROSS-REFERENCE

This application claims priority to German Application 101 35 073.2 filed Jul. 18, 2001, which disclosure is hereby incorporated herein by reference.

BACKGROUND AND SUMMARY

The present disclosure relates to a method of controlling and/or regulating a centrifuge for the centrifugal production of a milk product. It also relates to a system for implementing the method.

It is known to, for example, separate milk into skimmed milk and cream by centrifuges. Disk separators are generally used for this purpose.

During the separation into skimmed milk and cream, it is a goal of the centrifugal separation to minimize the fat content in the skimmed milk as much as possible in order to design the economical yield of the method to be as optimal as possible.

Unfortunately, the determination of the fat content of cream or skimmed milk is relatively problematic since the skimmed milk or the cream have a white coloring, so that methods for determining the light transmittance of the skimmed milk are high-expenditure (laboratory) processes, such as the process by Röse-Gottlieb and the process by Mojonier with precisions or a reproducibility of 0.03% and 0.015%.

The present disclosure provides for a method of controlling and/or regulating a centrifuge for the centrifugal production of a milk product as well as a system for implementing the method. The controlling and/or regulating of the centrifuge is simplified and a determination of the fat content becomes possible which is as precise as possible, and is simpler in comparison to the known laboratory processes and is independent of the latter.

Thus, the present disclosure relates to a method of controlling a centrifuge for the centrifugal production of a milk product. The method steps comprise: taking a milk sample at an outlet of the centrifuge from a liquid phase; adding a substance to the milk sample that increases light transmittance of the milk sample; determining the light transmittance of the milk sample by transilluminating the milk sample using a light source and measuring light intensity via a photo cell; determining fat content of the milk sample from a measurement of the light transmittance; and controlling the centrifuge as a function of the determination of the fat content.

The liquid phase from which the mild sample is taken may be skimmed milk. Furthermore, it should be noted that, by adding the substance, such as a suitable alkaline solution, to the milk sample, the pH-value is increased. It then becomes possible in a simple manner to increase the light transmittance of the white milk sample to such an extent that surprisingly it is possible to use an optical method for determining the fat content. The determination of the fat content can be carried out in intervals by a computer in an automated manner. If the computer, in turn, is connected with the control inputs of the actual centrifuge control, or the computer is even used for controlling the centrifuge, it becomes possible to utilize the information not only for monitoring the setting of the centrifuge but also for its controlling and/or also for the regulating as a function of the determination of the fat content. However, a manual monitoring by a person reading a display unit can also be implemented.

The light transmittance of the liquid phase, particularly of the skimmed milk, is increased in that the substance increasing the pH-value is proportioned and added such that the pH-value of the milk sample is increased to 11–14, preferably 12–13, and particularly to 13.

The present disclosure also relates to a system for controlling a centrifuge for the centrifugal production of a milk product. The system includes a device that takes a milk sample from a liquid phase at an outlet of the centrifuge. Also included is a device that adds a substance to the milk sample that increases light transmittance of the milk sample. Further included is a device that determines the light transmittance of the milk sample and from which a fat content of the milk sample is determinable. With regard to the system, it can be constructed, for example, as a separate unit and assigned to or connected with the centrifuge. Further, a device for controlling and/or regulating the setting of the centrifuge as a function of the determined fat content may be preferably assigned to or connected with the device for determining the light transmittance.

Other aspects of the present disclosure will become apparent from the following descriptions when considered in conjunction with the accompanying drawings.

DETAILED DESCRIPTION OF THE DRAWINGS

Figure 1:
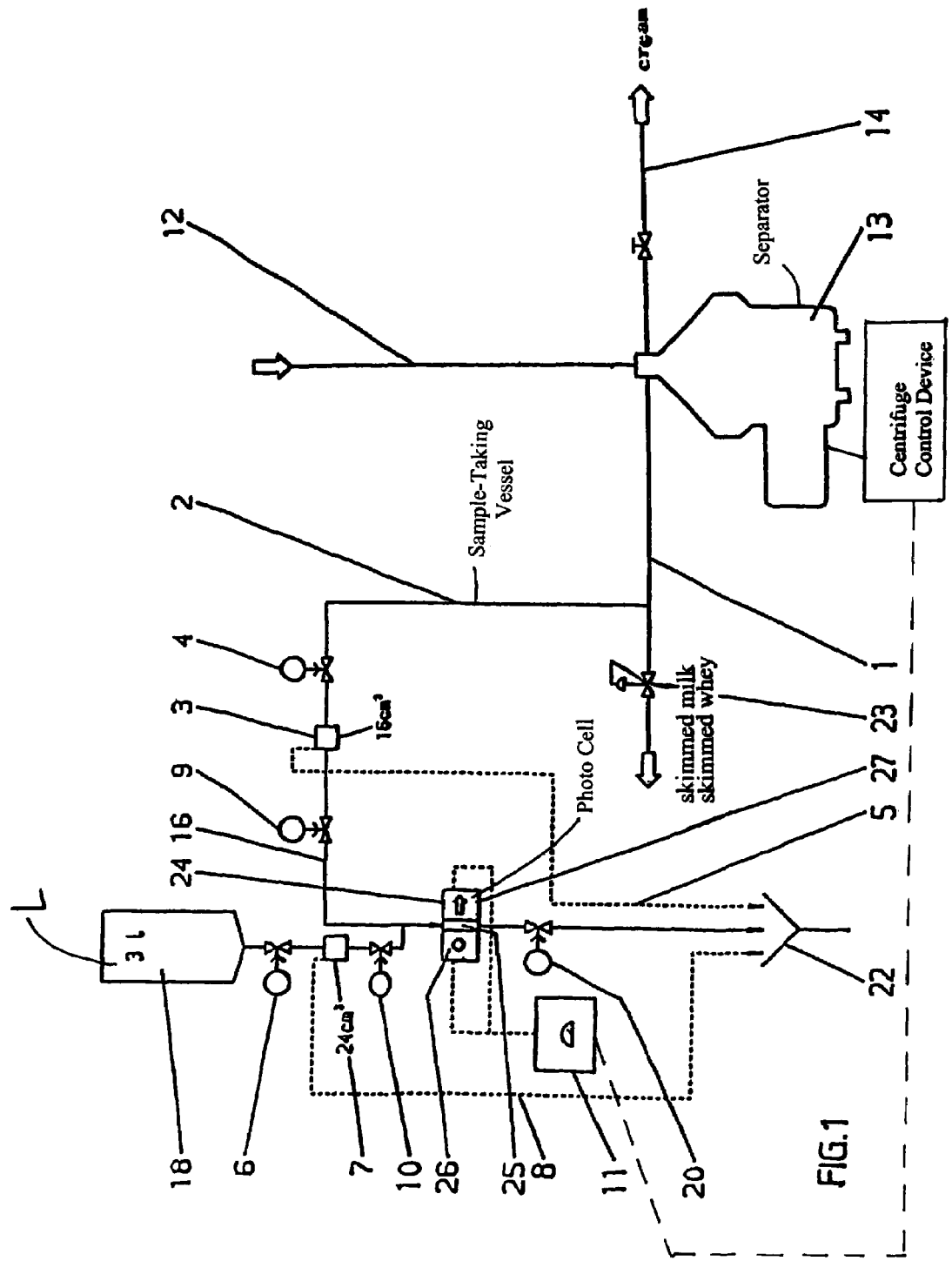
FIG. 1 is a schematic view of a system for controlling a centrifuge, according to the present disclosure.

FIG. 1 illustrates a centrifuge constructed as a disk separator 13 which has an inlet 12 for milk product 28 as well as an outlet 14 for cream and an outlet 1 for skimmed milk and skimmed whey. After centrifugal separation of the inflowing milk product 28 into cream and skimmed milk, it is possible to take skimmed milk from the outlet 1 of the centrifuge by way of a sample-taking pipe 2 connected into the outlet 1 of the centrifuge 13 and to guide this skimmed milk into a first storage tank 3. The removal takes place in front of a regulating or constant-pressure valve 23 assigned to or connected behind the centrifuge 13 in order to take the skimmed milk sample from a largely foam-free area.

A valve 4 is connected in front of the storage tank 3 and, when the first storage tank 3 is being filled, is opened until skimmed milk exits by way of a vent pipe 5 which is assigned to or connected with the first storage tank 3 and leads into collecting vessel 22. The size of the first storage tank 3 determines a volume which is required or used for measurements.

Another valve 9 for letting off the skimmed milk sample from the first storage tank 3 is connected behind the first storage tank 3. The valve 9 at the outlet of the first storage tank 3 is connected by way of a line 16 with a measuring cell 24 which may be an optical measuring cell, and which includes a sample-taking vessel 25, a light source 26 and a photo cell 27. The measuring cell 24 is connected with an analyzing and/or display device 11 (such as a computer, which also controls the measurements).

In addition, from a second storage tank 18, a liquid L or other substance (not shown) for increasing the pH-value of the milk sample discharged from the first storage tank 3 is connected in front of the measuring cell 24. From the second storage tank 18, the liquid L increasing the pH-value or the other substance increasing the pH-value, can be guided by way of an automatic valve 6 into a third storage tank 7. Again, the size of the third storage tank 7 determines the required volume. The third storage tank 7 is filled when liquid exits from an overflow bore or pipe 8 which is assigned to the third storage tank 7 and leads into the collecting vessel 22.

As soon as the two storage tanks 7 and 3 have been filled, the valves 9 and 10 connected behind the two storage tanks 7 and 3 are opened. This has the result that the liquids contained in the storage tanks 3 and 7 flow by way of the valves 9 and 10 into the sample-taking vessel 25 and are mixed there. By the addition of the liquid or substance from the third storage tank 7, the pH-value of the skimmed milk is increased such that the structure of protein situated in the skimmed milk is altered such that a light transmittance of the milk sample is achieved.

A quantitative proportion from the storage tanks 3 and 7 may be 2:3, when a suitable alkaline solution is used as the liquid or substance for increasing the pH-value.

From the previously-mentioned light transmittance, a residual fat content can now be determined. For this purpose, the light transmittance is determined, which takes place by irradiating the milk sample by the light source 26 and the photo cell 27 arranged relative to the light source 26 behind the measuring cell 24.

Figure 3:
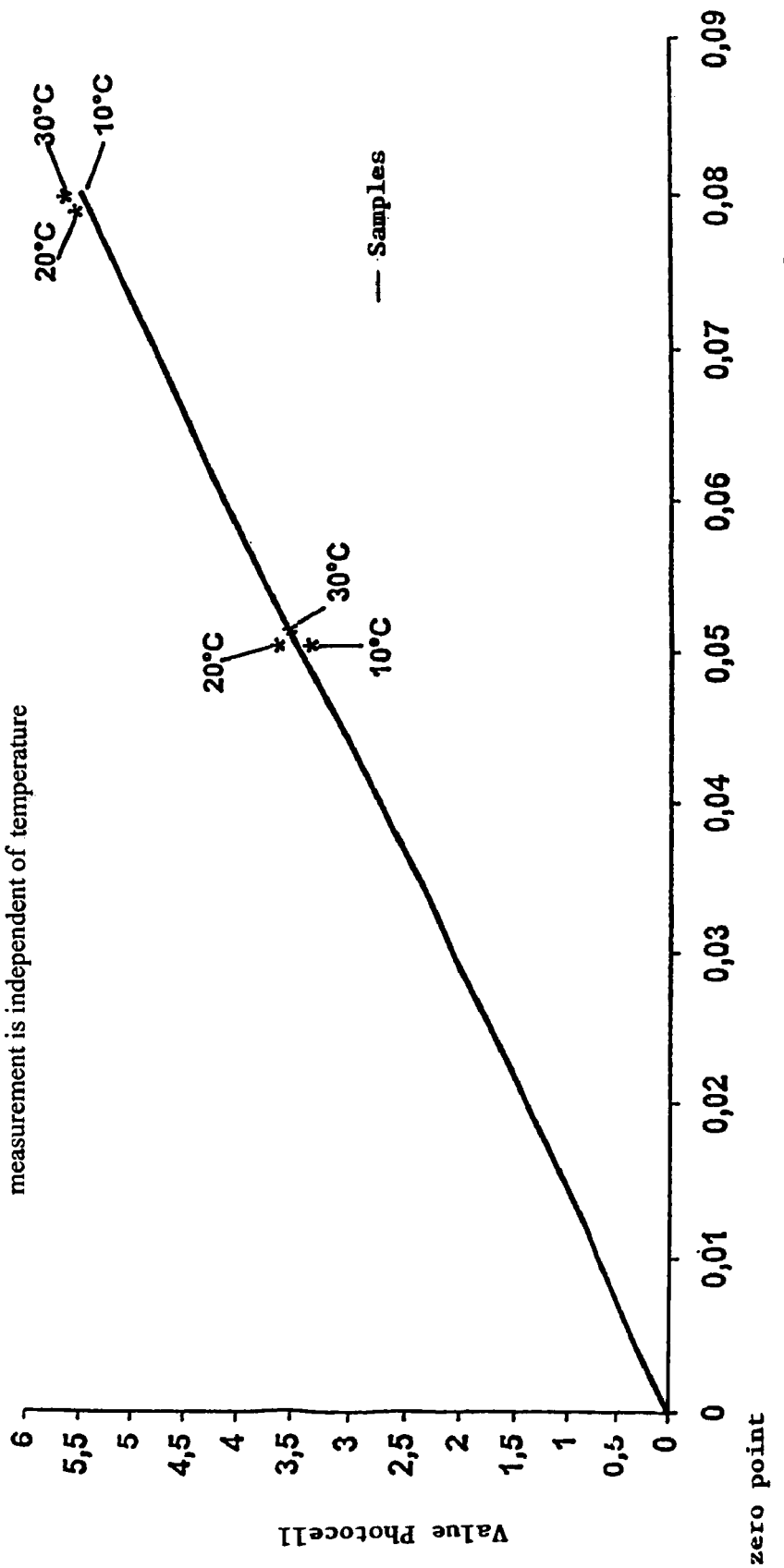
FIG. 3 is a diagram illustrating a ratio of the fat content to display value of the photo cell, according to the present disclosure.

Empirically, a corresponding table can be determined which indicates the dependence of the light transmittance on the residual fat content. The table can then be stored in a computer, so that, after the measuring of the light transmittance of the milk sample, the cloudiness and thus the fat content are determined by a comparison with the stored table. By a corresponding adjustment, it is even conceivable to provide the analyzing and/or display device 11 directly with a scale which indicates the residual fat content when a display is implemented which is proportional to the light transmittance. In this manner, the analysis of the determination of the fat content is further simplified. FIG. 3, which illustrates that the measurements are independent of the temperature and indicates the proportionality between the photo cell 27 display and the residual fat content, demonstrates that this display can be implemented.

Weak, almost crystal-clear skimmed milk samples have, for example, a residual content of approximately 0.05% fat. In contrast, considerable cloudiness indicates a residual fat content of approximately 0.15%.

After the measurement of the light transmittance, the milk sample is discharged from the measuring cell 24, for example, by way of a valve 20, into the collecting vessel 22.

Using the measurement, a setting of the centrifuge can be changed in the event of deviations from a desired value either manually or automatically, for example, by a computer (not shown here) connected to the measuring cell 24 and the disk centrifuge 13.

Figure 2:
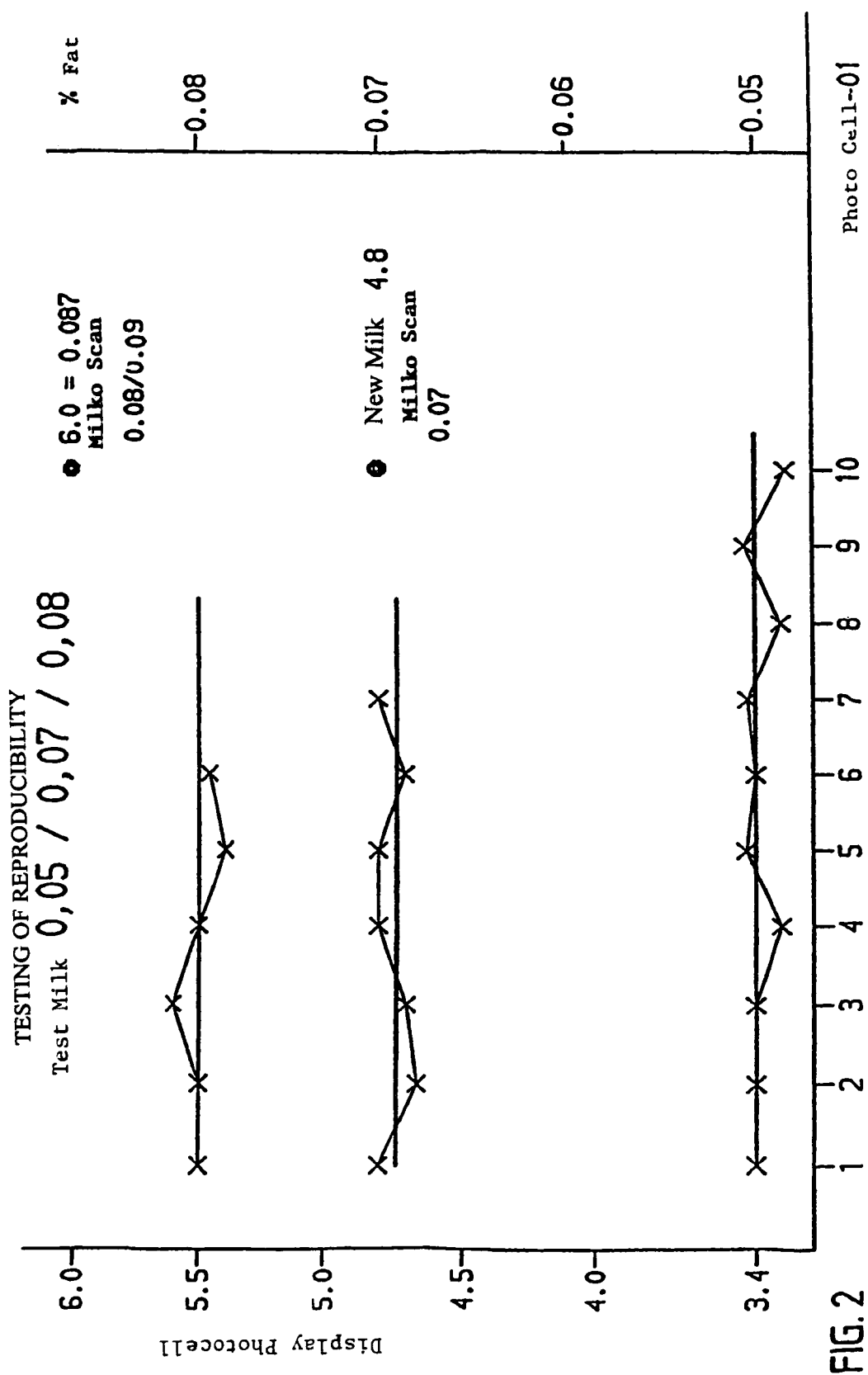
FIG. 2 is a diagram illustrating the testing of reproducibility of selected test results, according to the present disclosure.

FIG. 2 shows that a reproducibility can be achieved within a range of 1/1,000. This precision permits the usage of the present measuring method for controlling and/or regulating separators. In the case of a deterioration of the skimming value, a complete evacuation or a CIP (cleaning in place), for example, can be carried out. A reproducibility of less than 0.005% may possibly even be realistic.

Although the present disclosure has been described and illustrated in detail, it is to be clearly understood that this is done by way of illustration and example only and is not to be taken by way of limitation. The scope of the present disclosure is to be limited only by the terms of the appended claims.

The invention claimed is:

1. A method of controlling a centrifuge for the centrifugal production of a skimmed milk product, the steps comprising:
   taking a skimmed milk sample at an outlet of the centrifuge from a liquid phase;
   adding a substance to the skimmed milk sample that increases light transmittance of the skimmed milk sample;
   determining the light transmittance of the skimmed milk sample by transilluminating the skimmed milk sample using a light source and measuring light intensity via a photo cell;
   determining the fat content of the skimmed milk sample from a measurement of the light transmittance, the determining being done in an automated manner at intervals using a computer;
   providing a centrifuge control device connected to the centrifuge; and
   controlling the centrifuge, using the control device, as a function of the determination of the fat content while the light transmittance of the skimmed milk sample is determined.

2. The method according to claim 1, wherein the light transmittance of the skimmed milk sample is increased by the substance increasing the pH-value of the skimmed milk sample.

3. The method according to claim 2, wherein the pH-value is proportioned and added such that the pH-value of the skimmed milk sample is increased to 11–14.

4. The method according to claim 2, wherein the pH-value is proportioned and added such that the pH-value of the skimmed milk sample is increased to 12–13.

5. The method according to claim 2, wherein the pH-value is proportioned and added such that the pH-value of the skimmed milk sample is increased to 13.

6. A system for controlling a centrifuge for the centrifugal production of a skimmed milk product, comprising:
   a first device configured to take a skimmed milk sample from a liquid phase at an outlet of the centrifuge, the first device including a sample-taking pipe and a first storage tank;
   a second device configured to add a substance to the skimmed milk sample that increases light transmittance of the skimmed milk sample, the second device including a second storage tank and a valve;
   a third device configured to determine the light transmittance of the skimmed milk sample and from which a fat content of the skimmed milk sample is determinable, the third device including a measuring cell including a sample-taking vessel, a light source, and a photocell, and the third device using a computer to determine the fat content of the skimmed milk sample at intervals in an automated manner; and
   a fourth device including a control device configured to be connected to control the centrifuge as a function of the determined fat content.

7. The system according to claim 6, wherein the fourth device is connected with the third device configured to determine the light transmittance.

8. The system according to claim 6, further including a first valve leading into the first storage tank, the sample-taking pipe and first valve being connected with the outlet of the centrifuge.

9. The system according to claim 6, wherein the sample-taking pipe is connected in front of a constant pressure valve.

10. The system according to claim 6, wherein the first storage tank is connected via a second valve with the measuring cell.

11. The system of claim 10, wherein at least one of an analyzing device and a display device is connected with the measuring cell.

12. The system according to claim 6, wherein the second storage tank is configured to receive a substance for increasing the pH-value of the skimmed milk sample and is connected in front of the measuring cell.

13. The system according to claim 6, wherein at least one of an analyzing device and a display device is connected with the measuring cell.

14. The system according to claim 13, wherein the at least one of the analyzing device and the display device is provided with a scale which directly displays a residual fat content of the skimmed milk sample.

15. The system according to claim 6, wherein the system is a separate measuring unit which is connected with the centrifuge.

16. The system of claim 6, wherein the centrifuge is a disk separator.

17. The system of claim 6, wherein the measuring cell includes an optical measuring cell.

* * * * *